(12) United States Patent
Spector et al.

(10) Patent No.: US 10,660,991 B2
(45) Date of Patent: May 26, 2020

(54) POLYMERIC DHA-CONTAINING BIODEGRADABLE COMPOSITIONS AND SURGICAL BARRIER DEVICES MADE THEREOF

(71) Applicant: CORNELL UNIVERSITY, Ithaca, NY (US)

(72) Inventors: Jason A. Spector, New York, NY (US); David A. Putnam, Ithaca, NY (US); Nicole Ricapito, Putnam Valley, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 39 days.

(21) Appl. No.: 16/090,969

(22) PCT Filed: Apr. 7, 2017

(86) PCT No.: PCT/US2017/026512
§ 371 (c)(1),
(2) Date: Oct. 3, 2018

(87) PCT Pub. No.: WO2017/177088
PCT Pub. Date: Oct. 12, 2017

(65) Prior Publication Data
US 2019/0117853 A1    Apr. 25, 2019

Related U.S. Application Data

(60) Provisional application No. 62/319,593, filed on Apr. 7, 2016.

(51) Int. Cl.
| | | |
|---|---|---|
| *A61L 31/14* | (2006.01) | |
| *C08G 64/18* | (2006.01) | |
| *A61K 31/765* | (2006.01) | |
| *A61B 17/04* | (2006.01) | |
| *A61B 17/34* | (2006.01) | |
| *C08L 69/00* | (2006.01) | |

(52) U.S. Cl.
CPC ............ *A61L 31/148* (2013.01); *A61B 17/04* (2013.01); *A61B 17/3494* (2013.01); *A61K 31/765* (2013.01); *C08G 64/183* (2013.01); *C08L 69/00* (2013.01); *C08G 2230/00* (2013.01); *C08L 2201/06* (2013.01); *C08L 2203/02* (2013.01)

(58) Field of Classification Search
CPC .... A61B 17/3494; A61K 31/765; C08L 69/00
See application file for complete search history.

(56) References Cited

U.S. PATENT DOCUMENTS

| | | |
|---|---|---|
| 7,659,420 B2 | 2/2010 | Putnam et al. |
| 8,916,143 B2 | 12/2014 | Putnam et al. |
| 2007/0123689 A1 | 5/2007 | Hossainy et al. |
| 2008/0194786 A1 | 8/2008 | Putnam et al. |
| 2015/0079019 A1 | 3/2015 | Putnam et al. |

OTHER PUBLICATIONS

Extended European Search Report dated Nov. 7, 2019 issued in European Patent Application 1779882.4.
Zawaneh P. et al., "Diblock Copolymers Based on Dihydroxyacetone and Ethylene Glycol: Synthesis, Characterization, and Nanoparticle Formulation", Biomacromolecules 7:3245-3251 (2006).
International Search Report dated Jun. 27, 2017 issued in PCT/US2017/026512.
Henderson P.W. et al., "A rapidly resorbable hemostatic biomaterial based on dihydroxyacetone", Journal of Biomedical Materials Research Part A, (2009), pp. 776-782 DOI: 10.1002/jbm.a.32586.
Ricapito N.G. et al., "Insight into the Unexpectedly Rapid Degradation of Dihydroxyacetone-Based Hydrogels", Macromolecular Chemistry and Physics, (2016), 217, pp. 1917-1925 DOI: 10.1002/macp.201600170.

*Primary Examiner* — Andrew S Rosenthal
(74) *Attorney, Agent, or Firm* — Scully, Scott, Murphy & Presser, P.C.

(57) ABSTRACT

Polymer compositions having the following chemical structure: wherein $L^1$ represents a polymeric linker having the structure shown connecting ethylene oxide oligomers and their use in surgical devices containing the above composition is also described.

28 Claims, 2 Drawing Sheets

POLYMERIC DHA-CONTAINING BIODEGRADABLE COMPOSITIONS AND SURGICAL BARRIER DEVICES MADE THEREOF

CROSS REFERENCE TO RELATED APPLICATION

This application claims the benefit of priority from U.S. Provisional Application No. 62/319,593, filed on Apr. 7, 2016.

FIELD OF THE INVENTION

The present invention relates generally to elastomeric flexible compositions useful as surgical barrier materials, as well as surgical materials and devices that are biodegradable.

BACKGROUND OF THE INVENTION

Laparotomy, or surgical entry into the peritoneal cavity for abdominal surgery, is one of the most common surgical procedures performed in the United States with an estimated 4 million cases performed annually, with millions more performed worldwide. Closure of the peritoneal cavity after abdominal surgery requires careful re-approximation of the fascia (the strength layer of the abdominal wall) in order to minimize the risk of incisional hernia. Injury to the bowel during fascial closure, and the associated morbidity or mortality, may occur as a result of insufficient visualization during closure, leading to either direct needle puncture of the bowel or strangulation by suture as it is tightened out of the view of the surgeon. Currently, intraoperative maneuvers used to prevent visceral injury include use of a metal malleable retractor or the PVC Glassman Visceral Retainer to displace and shield the bowel. However, these strategies are only partially effective as neither device completely shields the viscera. More problematically, they must be removed from the peritoneal cavity prior to closure of the final few centimeters of fascia, leaving the bowel unprotected and vulnerable to injury during this most crucial phase of the operation. Inadequate visualization and protection of the bowel further contribute to increased rates of hernia recurrence as surgeons may incorporate suboptimal fascial "bites" to decrease the risk of bowel injury during closure. The mass of bowel is also typically wider than the retractor, which leads to ineffective displacement Another commonly used instrument in abdominal surgery is the Glassman Visceral Retractor or "FISH". This flexible device is used to shield the bowel from inadvertent injury and is quite popular. However, because the "FISH" device is made of plastic, it must be removed from the peritoneal cavity prior to tying the final several sutures, leading to "blind" suture tying, which often results in bowel loops becoming ensnared. Further, the device is often not wide enough to prevent bowel from entering the surgical field, a design flaw resulting from the need to keep it thin enough so that it can be removed from the peritoneal cavity through a relatively small opening prior to tying of the last several fascial sutures. Ultimately, the major drawback to both the current malleable retractor and "FISH," respectively, is the inherent risk they pose as retained instruments during abdominal surgery, which leads to significant postoperative morbidities, including bowel obstruction, perforation, sepsis, reoperations, and even death. In fact, retained surgical instruments are exceedingly common with an incidence between 0.3 and 1.0 per 1,000 abdominal operations despite their avoidable nature (e.g., Stawicki, S. P., et al., Retained surgical foreign bodies: A comprehensive review of risks and preventive strategies, *Scand. J. Surg.* 2009, 98, 8-17).

Furthermore, beyond the difficulty posed by fascial closure, post-operative bowel adhesions (the pathologic fibrotic bands that commonly develop after surgical manipulation), are a significant contributor to patient morbidity and mortality. To enumerate, abdominal post-operative adhesions occur in an alarming 90% of abdominal surgery patients, and are a major cause of bowel obstruction, bowel perforation, chronic pelvic pain, and infertility. Medical complications from abdominal adhesions are extraordinarily high with between 30% and 75% of abdominal surgery patients requiring secondary surgery to correct conditions directly related to adhesion formation, with the economic cost of abdominal tissue adhesions and their treatment exceeding $2.1 billion annually in the United States alone (e.g., Ellis, H., et al., Adhesion-related hospital readmissions after abdominal and pelvic surgery: a retrospective cohort study. *Lancet.* 1999, 353, 1476-1480; Ray, N. F. et al., Abdominal adhesiolysis: inpatient care and expenditures in the United States in 1994. *J Am Coll Surg.* 1998, 186, 1-9. Given the above limitations of surgical instruments currently employed in abdominal surgery, there would a significant benefit in a surgical barrier that could reduce the complications associated with abdominal surgery and to better facilitate fascial closure.

SUMMARY OF THE INVENTION

The invention is directed, in a first aspect, to polymeric compositions that possess a combination of strength (particularly, resistance to needle puncture) and flexibility such that the compositions are ideally suited as protective shields during surgery. A significant advantage of the polymeric compositions described herein is their ability to degrade within bodily tissue, thereby advantageously eliminating the need for their removal after surgery. Indeed, as further discussed in this application, the material can completely degrade very rapidly (i.e., within 3-24 hours) and be eliminated from the body. Hence, the risks associated with device removal are eliminated. A further advantage of the polymeric compositions described herein is their substantial lack of toxicity during degradation in the body. The polymeric compositions described herein include glycerolate and dihydroxyacetone (DHA) components, both of which are generally regarded as safe and non-toxic in the body.

The polymeric compositions described herein possess at least two unique features: 1) the capacity to be processed into thin wafers with sufficient flexibility and the resistance to withstand inadvertent needle puncture; and 2) a rapid degradation profile in aqueous environments, such as the intraperitoneal cavity, e.g., a 96% degradation after 4 hours when in contact with bodily fluid. Given these properties, these polymeric compositions can be utilized across multiple surgical disciplines, including their use as rapidly degradable surgical shields to protect the bowel during laparotomy closure and potentially mitigate formation of post-operative bowel adhesions. These polymeric compositions can also be used in a number of surgical settings beyond abdominal or laparotomy surgery.

The biodegradable polymeric compositions are represented by the following chemical structure:

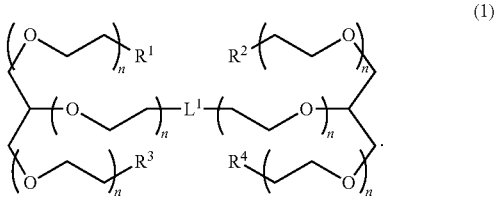

(1)

In Formula (1), $L^1$ represents a polymeric linker having the following structure:

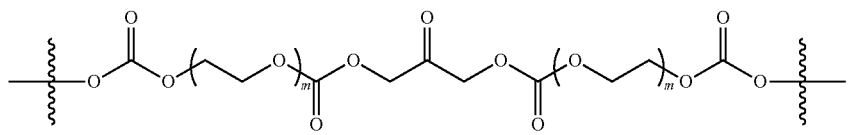

and $R^1$, $R^2$, $R^3$, and $R^4$ are —OR', wherein R' is independently selected in each instance from hydrogen atom and hydrocarbon groups containing 1-6 carbon atoms and optionally containing one or more heteroatoms selected from N, O, S, and halogen atoms. $R^1$ and $R^2$ are optionally interconnected to form a polymeric linker $L^2$, and/or $R^3$ and $R^4$ are optionally interconnected to form a polymeric linker $L^3$, wherein $L^2$ and $L^3$ are each independently represented by the structure provided for $L^1$, except that the subscript m is taken independently among $L^1$, $L^2$, and $L^3$. The subscript n is an integer of at least 2, and the subscript m is an integer of at least 2 and up to 10.

In particular embodiments, the composition of Formula (1) has the following sub-generic chemical structure:

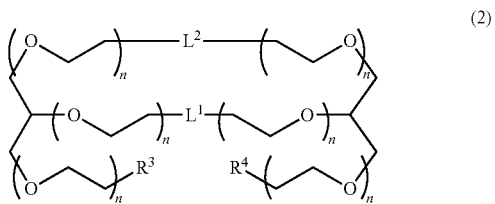

(2)

In more particular embodiments, the composition of Formula (1) has the following sub-generic chemical structure:

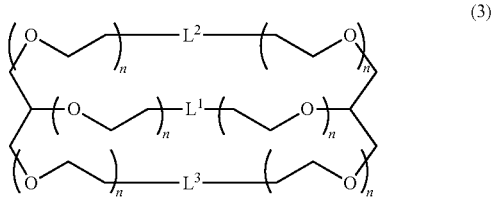

(3)

In a second aspect, the invention is directed to a surgical barrier device capable of shielding biological tissue from inadvertent needle puncture and capable of biodegrading in the biological tissue after use, the surgical barrier device containing a film of the polymeric biodegradable composition described above according to Formulas (1), (2), or (3). The film can have a thickness of, for example, at least 0.5 mm and up to 5 mm, or a thickness of at least 1 mm or 2 mm and up to 5 mm, or a thickness of at least 1 mm or 2 mm and up to 3 mm.

In a third aspect, the invention is directed to a method for producing the biodegradable polymeric composition according to Formulas (1), (2), or (3). The method generally involves polymerizing a glycerol alkoxylate (e.g., glycerol ethoxylate), a polyalkylene glycol bis(chloroformate), and DHA monomer. The molar ratio of glycerol alkoxylate to DHA monomer is typically 1:1-2, or more particularly, 1:1.5. The molar ratio of glycerol alkoxylate to polyalkylene glycol bis(chloroformate) it typically about 2.5-3.5:1, or more typically, about 3:1. The molar ratio of DHA monomer to polyalkylene glycol bis(chloroformate) is typically about 2.5-3.5:1, or more typically, about 5:1. Typically, the components are reacted in a polar aprotic organic solvent (e.g., pyridine) at reduced temperature, generally less than 10° C. and above the freezing point of the solvent.

In a fourth aspect, the invention is directed to a method of protecting bodily tissue from needle puncture during surgery. In the method, a surgical barrier device capable of shielding biological tissue from inadvertent needle puncture is placed on bodily tissue to be protected during surgery. The surgical barrier device is as described above, i.e., containing a film of the polymeric biodegradable composition described above according to Formulas (1), (2), or (3).

BRIEF DESCRIPTION OF THE FIGURES

FIG. 2A: Plot showing the results of a mechanical test using unconfined compression of six 8-mm diameter, 2 mm-thick CC-DHA shields (average Young's modulus was 46.4+/−9.23 kPa). FIG. 2B. Plot showing the results of a mechanical test using puncture with GS 21 surgical needle on the CC-DHA shield, rubber band, and rat bowel.

DETAILED DESCRIPTION OF THE INVENTION

Figure 1:
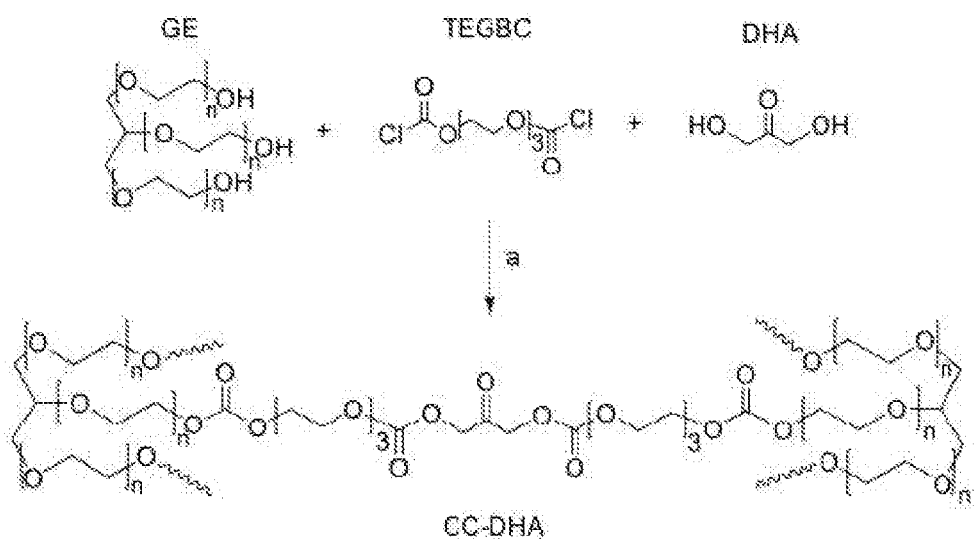
FIG. 1. Synthetic scheme for preparing CC-DHA polymer elastomer networks. Step (a) includes chloroform, pyridine, on ice, 3 hours. Nomenclature: GE: glycerol ethoxylate; TEGBC: tri(ethylene glycol) bis(chloroformate); DHA: dihydroxyacetone; CC-DHA: chemically crosslinked dihydroxyacetone-based hydrogel. The wavy lines indicate the presence of additional linking moieties having the structure shown in the central portion of the CC-DHA final structure.

In one aspect, the invention is directed to a polymeric composition containing a glycerolate moiety, carbonate linkages, a polyalkylene oxide moiety, and crosslinked DHA. The polymeric composition is advantageously flexible and elastomeric, yet of sufficient strength to block a needle puncture to underlying tissue. The polymeric composition is also advantageously biodegradable and non-toxic, thereby permitting the composition, when used as a shield, to naturally degrade within the body without adverse effect. By virtue of the biodegradable property of the polymeric composition, the surgeon can advantageously dispense with a post-operative procedure of extracting the surgical barrier device.

The composition has the following generic chemical structure:

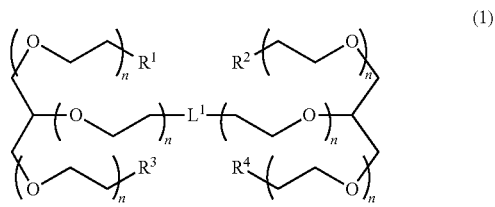

(1)

In Formula (1), $L^1$ represents a polymeric linker having the following structure, wherein the wavy lines indicate points of attachment of the linker in Formula (1):

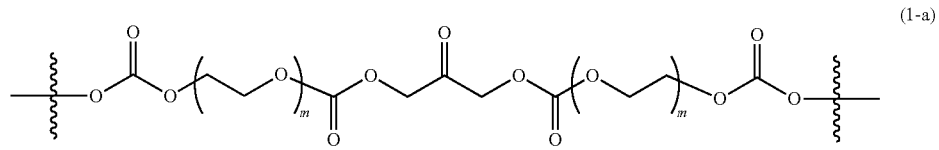

(1-a)

In Formula (1), $R^1$, $R^2$, $R^3$, and $R^4$ are each represented by the group —OR', wherein R' is independently selected in each instance from hydrogen atom and hydrocarbon groups containing 1-6 carbon atoms and optionally containing one or more heteroatoms selected from N, O, S, and halogen atoms. When R' is hydrogen atom (H), then —OR' is a hydroxy (—OH) group. When R' is a hydrocarbon group, then —OR' is an alkoxy group, which may be the same or different alkoxy group among $R^1$, $R^2$, $R^3$, and $R^4$. The hydrocarbon group (as R') can independently contain, for example, 1, 2, 3, 4, 5, or 6 carbon atoms, or a number of carbon atoms within a range therein.

The hydrocarbon group (as R') can, in one embodiment, lack heteroatoms, i.e., be composed solely of carbon and hydrogen atoms. The no-heteroatom hydrocarbon group can be, for example, straight-chained or branched versions of alkyl, alkenyl, and alkynyl groups; cycloalkyl groups; cycloalkenyl groups; and phenyl groups. Some examples of straight-chained alkyl groups include methyl, ethyl, n-propyl, n-butyl, n-pentyl, and n-hexyl groups. Some examples of branched alkyl groups include isopropyl (2-propyl), isobutyl (2-methylprop-1-yl), sec-butyl (2-butyl), t-butyl, 2-pentyl, 3-pentyl, 2-methylbut-1-yl, isopentyl (3-methylbut-1-yl), 1,2-dimethylprop-1-yl, 1,1-dimethylprop-1-yl, neopentyl (2,2-dimethylprop-1-yl), 2-hexyl, 3-hexyl, 2-methylpent-1-yl, 3-methylpent-1-yl, and isohexyl (4-methylpent-1-yl) groups, wherein the "1-yl" suffix represents the point of attachment of the group. Some examples of cycloalkyl groups include cyclopropyl, cyclobutyl, cyclopentyl, and cyclohexyl groups. Some examples of straight-chained alkenyl groups include vinyl, propen-1-yl (allyl), 1-buten-4-yl (CH$_2$═CH—CH$_2$—CH$_2$—), 2-buten-4-yl (CH$_2$—CH═CH—CH$_2$—), butadienyl, and 1-penten-4-yl groups. Some examples of branched alkenyl groups include propen-2-yl, 1-buten-3-yl (CH$_2$═CH—CH.—CH$_3$), 1-buten-2-yl (CH$_2$═C.—CH$_2$—CH$_3$), 1-penten-4-yl, 1-penten-3-yl, 2-penten-4-yl, 2-penten-3-yl, and 1,3-pentadien-3-yl groups, wherein the dot in the foregoing exemplary formulas represents the point of attachment of the group. Some examples of cycloalkenyl groups include cyclopropenyl, cyclobutenyl, cyclopentenyl, cyclopentadienyl, cyclohexenyl, and cyclohexadienyl groups.

The hydrocarbon group (as R') can, in another embodiment, include heteroatoms selected from N, O, S, and halogen atoms (e.g., F, Cl, Br, or I atoms). When the above-described hydrocarbon groups having 1 to 6 carbon atoms are permitted to include one or more heteroatoms, the hydrocarbon group may contain at least one heteroatom that interrupts a carbon-carbon bond, e.g., —O— or —S— interrupting a carbon-carbon bond to form an ether or thioether group. Alternatively, the heteroatom may interrupt a carbon-hydrogen bond, e.g., —O— or —S— interrupting a carbon-hydrogen bond to form an alcohol or thiol group.

In the case of a halogen atom, this may replace a hydrogen atom residing on a carbon atom. In the case of O and S, the heteroatom may replace two hydrogen atoms residing on a carbon atom to result in, for example, a ketone or thioketone. In other embodiments, a heteroatom-containing group can replace a hydrogen atom in the hydrocarbon group. The heteroatom-containing group can be, for example, —OR; —SR; —OC(O)R; —C(O)OR; —C(O)NR$_2$; —N(R)C(O)R; or —NR$_2$, wherein R is independently a hydrogen atom or non-heteroatom-containing hydrocarbon group containing 1-6 carbon atoms, as described above.

In some embodiments of Formula (1), $R^1$ and $R^2$ (or $R^3$ and $R^4$) are interconnected to form a polymeric linker $L^2$, wherein L2 is independently represented by the structure provided for $L^1$, except that the subscript m is taken independently among $L^1$ and $L^2$. The resulting structure is provided by the following sub-generic structure:

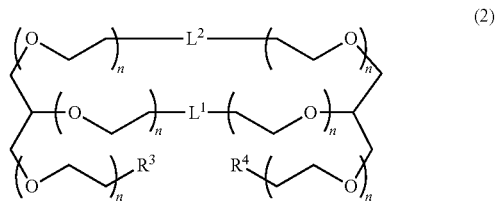

(2)

In some embodiments of Formula (1), $R^1$ and $R^2$ are interconnected as $L^2$, as above in Formula (2), and $R^3$ and $R^4$ are also interconnected to form a polymeric linker $L^3$, wherein $L^2$ and $L^3$ are each independently represented by the structure provided for $L^1$, except that the subscript m is taken independently among $L^1$, $L^2$, and $L^3$. The resulting structure is provided by the following sub-generic structure:

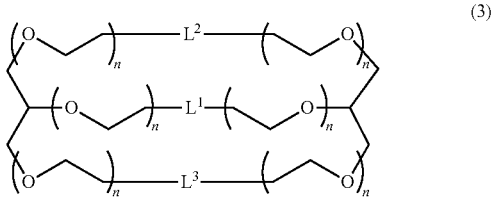

(3)

The subscript n is an integer of at least 2. In various embodiments, the subscript n is an integer of precisely or at least 2, 3, 4, 5, 6, 7, 8, 9, 10, 12, 15, 20, 30, 40, 50, 60, 70, 80, 90, 100, 150, 200, 250, or 300, or a value within a range bounded by any two of the foregoing values.

The subscript m is an integer of at least 2 and up to 10. In various embodiments, the subscript m is an integer of precisely, 2, 3, 4, 5, 6, 7, 8, 9, or 10, or a value within a range bounded by any two of the foregoing values, e.g., at least 2 or 3, and up to 4, 5, 6, 7, 8, 9, or 10.

In another aspect, the invention is directed to methods for producing the polymeric compositions described above. The method generally involves polymerizing a glycerol alkoxylate (e.g., glycerol ethoxylate or glycerol propoxylate), a polyalkylene glycol bis(chloroformate), and DHA monomer. The polyalkylene glycol is typically a polyethylene glycol (PEG), but in some embodiments may be, for example, a polypropylene glycol or polybutylene glycol. The molar ratio of glycerol alkoxylate to DHA monomer is typically 1:1-2, or more particularly, 1:1.5. The molar ratio of glycerol alkoxylate to polyalkylene glycol bis(chloroformate) it typically about 2.5-3.5:1, or more typically, about 3:1. The molar ratio of DHA monomer to polyalkylene glycol bis (chloroformate) is typically about 2.5-3.5:1, or more typically, about 5:1. Typically, the components are reacted in a polar aprotic organic solvent (e.g., chloroform or pyridine) at reduced temperature, generally less than 5° C. or 10° C. and above the freezing point of the solvent.

In another aspect, the invention is directed to a surgical barrier device capable of shielding biological tissue from inadvertent needle puncture and capable of biodegrading in the biological tissue after use. The surgical barrier device is or includes a film of any of the compositions described above under Formulas (1), (2), or (3). The film generally has a thickness of at least 0.5, 0.6, 0.7, 0.8, 0.9, or 1 mm, or a thickness within a range bounded by any of these two values. Generally, the film has a thickness of up to 2, 3, 4, or 5 mm, or a thickness within a range bounded by any of these two values. Alternatively, the film has a thickness between any of the minimum and maximum values provided above. As the film should be capable of protecting an area of bodily tissue during surgery, the film will generally have a diameter (or length) in one or both planar dimensions of at least 1, 2, 3, 4, or 5 centimeters. The invention also contemplates shapes other than a film, to render the elastomer useful for other or additional purposes, e.g., as a suture (i.e., thread), bandage, band, tube, or sleeve.

In one embodiment, the film is a monolith, and thus, not coated or layered with another material. In another embodiment, the film is coated or layered with another material, in which case the film can be considered a layer within a multi-layer composite. If another one or more layers are included, the additional layers should also be biodegradable.

In another aspect, the invention is directed to a method of protecting bodily tissue from needle puncture during surgery. In the method, a surgical barrier device, as described above, is placed on bodily tissue to be protected during surgery. At the completion of surgery, the surgical barrier device is left in the body, and the surgical barrier device is allowed to naturally degrade in the biological tissue and ultimately leave the body as degradation products. The surgical barrier device generally exhibits a degradation profile of at least 90%, 93%, 95%, or 97% degradation within 3, 4, 5, or 6 hours of contact of the surgical barrier device with bodily fluid. The surgery may be, for example, abdominal surgery, or more particularly, an abdominal surgery that includes fascial closure or a laparotomy. The surgery may also be other than abdominal surgery, such as heart surgery, coronary artery bypass surgery, tumor removal surgery, or organ transplant or removal surgery.

Examples have been set forth below for the purpose of illustration and to describe the best mode of the invention at the present time. However, the scope of this invention is not to be in any way limited by the examples set forth herein.

EXAMPLES

Preparation of DHA Monomer

DHA dimer was converted to monomeric form according to a previously published protocol (Ricapito N G, et al., Insight into the Unexpectedly Rapid Degradation of Dihydroxyacetone-Based Hydrogels, *Macromol. Chem. Phys.,* 2016 September; 217(17):1917-25). In brief, 400 mL of 2-propanol was combined with 12 g of DHA dimer and stirred for 70 minutes, while partially immersed in a 60° C. oil bath. The resulting solution was filtered and the volume reduced by roto-evaporation at 50-55° C. over 95 minutes or less, to result in removal of ~100 mL of 2-propanol. The remaining solution was held at −20° C. overnight to crystallize DHA in the monomeric form. The crystallized DHA was recovered by filtration, and dried under vacuum at room temperature to yield 6.15±0.62 g (n=3) of white material.

CC-DHA Hydrogel Synthesis

A general overview of the synthetic scheme for producing the CC-DHA hydrogels is provided in FIG. 1. In preparation, a custom-made cylindrical flask (OD: 41 mm, ID: 36.7 mm, height: 90 mm) and a 15 mm by 6 mm egg-shaped, Teflon-coated, stir bar were flame-dried, then cooled under a dry $N_2$ stream. A solution of glycerol ethoxylate (GE) (2.919 g, 0.00292 mol) and anhydrous chloroform (6 mL) was added. DHA monomer (0.394 g, 0.00438 mol) was carefully poured into the solution, resulting in a suspension due to the insolubility of DHA in chloroform. The flask was then lowered into an ice bath and stirred magnetically.

Subsequently, tri(ethylene glycol) bis(chloroformate) (1.8 mL, 0.0088 mol) was added dropwise over 6 minutes, followed by addition of pyridine (1.62 mL, 0.02 mol) over approximately 5.4 minutes. Pyridine was added to the bottom and sides of the reaction mixture using two separate 6-inch syringe needles, consecutively. Movement of the reaction flask across the stir plate during pyridine addition enabled the stir bar to access multiple points of the mixture and provided enhanced mixing of reagents. A gel began to form during the final stages of pyridine addition and the whole reaction appeared as a gel in approximately 10 minutes.

The gel was held for 1 hour on ice to ensure completion of the reaction, and then approximately 30 mL of diethyl ether was poured into the reaction flask to begin extraction of the solvent. After 30 minutes, the gel was slowly peeled from the glass edges using a spatula, after which the gel was allowed to sit submerged in the diethyl ether overnight at room temperature to continue the initial solvent extraction and prepare the gel for slicing.

Diethyl ether was then decanted from the reaction flask, the gel was removed, and the top surface was leveled using a standard razor and light sanding procedure. The gel was then sliced into 2 mm-thick sections. The gel slices were placed into 400 mL of chloroform for final purification by extraction with six chloroform exchanges over a minimum of 4 days. The gel was further purified through incubation in 25:75, 50:50, and 75:25 volume-to-volume solutions of diethyl ether and chloroform, respectively, for 10 minutes each, followed by 20 minutes in diethyl ether. Lastly, the gel was dried under vacuum for two nights at room temperature, washed briefly with MilliQ water, and lyophilized. The gel was formed into 8 mm shields using 8 mm biopsy punches. Masses ranged from 83.6+/−12.6 mg (n=30). Gels were stored in the presence of desiccant under dry $N_2$ at −20° C.

In Vivo Degradation Studies in a Murine Model

In vivo degradation of the CC-DHA shields 8 mm in diameter was tested in 10-week-old male C57BL/6N mice. Sixteen mice were anesthetized by an intraperitoneal injection of ketamine (150 mg/kg) and xylazine (15 mg/kg). Warmed normal saline (1 mL) was injected subcutaneously into the dorsum. The abdomen was depilated and prepped with alternating ethanol and betadine swabs. Then, a 2.5 cm vertical midline laparotomy was performed. CC-DHA shields (81.4±14.4 mg), were placed into the peritoneum in a sub-fascial position with the bowel subjacent. 6-0 polypropylene suture (Prolene™, 6-0 suture) was used to mark each shield to facilitate identification and removal of remaining hydrogel at specified time points. Peritoneum and fascia were closed using a single continuous running stitch with 5-0 nylon suture and sterile dressings applied. Anesthetic was reversed with atipamazole 20 mg intraperitoneal injection, and an additional 1 ml of warm normal saline was injected subcutaneously into the dorsum of each mouse. External heat was provided until animals were independently ambulatory. Incision, implantation, and suturing occurred consistently within 12 minutes.

Mice were euthanized at 3, 6, 9 and 24 hours post implantation (n=4 per group) and underwent repeat laparotomy to evaluate abdominal residual polymer shield weight at each time point. All animal care and experimental procedures were in compliance with the Guide for the Care and Use of Laboratory Animals. All animals were provided with chow and water ad libitum, and maintained in a climate-controlled facility accredited by the Association for Assessment and Accreditation of Laboratory Animal Care.

In Vivo Toxicity and Peritoneal Adhesion Studies

To evaluate possible long-term toxicity, peritoneal scarring and/or promotion of adhesions associated with CC-DHA elastomer implantation, C57BL/6N underwent laparotomy with intraperitoneal elastomer shield or saline placement. Sixteen 10-week-old male C57BL/6N mice underwent identical laparotomy procedure as described above. Eight mice had 8-mm shields (84.6+/−5.0 mg) placed over the midline viscera of the abdomen, while eight other mice received 0.5 mL saline injected over the viscera. Animals were evaluated daily over 14 days for evidence of well-being as noted by grooming, nesting, bowel movements, and ambulation. On day 14, mice were euthanized and underwent repeat laparotomy to evaluate their peritoneal cavity for evidence of adhesion formation via gross and histologic examination.

CC-DHA Hydrolysis and Metabolism Studies

The CC-DHA elastomer was rapidly hydrolyzed into dihydroxyacetone and various PEGs and GEs. DHA is a naturally occurring intracellular molecule and readily metabolized, whereas the PEGs, which include the GEs, are metabolically inert and can be readily detected by $^1$H NMR. Therefore, the fate of the PEGs was followed to evaluate peritoneal degradation products and excretion of the degradation products in the urine. Five 10-week-old C57BL/6N underwent midline laparotomy as described above. Three underwent placement of 8-mm shields (89.5+/−13.3 mg) over the viscera of the abdomen, while two mice received 0.5 mL saline injection over the viscera. Once recovered, animals were sacrificed at 3 hours and serum, urine, and peritoneal fluid were collected. If peritoneal fluid was less than 50 μL, an additional 400 μL was injected into abdomen over viscera and then collected.

For detection of soluble PEG using 1H NMR, samples of peritoneal fluid (200 μL) and serum (200 μL) were each diluted with 20 μL of 99.96% $D_2O$; samples of urine (100 μL) were each diluted with 100 μL of 99.96% $D_2O$. Spectra were recorded on a Varian™ UNITYINOVA spectrometer operating at 599.79 MHz for $^1$H observation using a 3 mm Varian™ inverse $^1H\{^{13}C,^{15}N\}$ triple resonance probehead equipped with triple axis gradient coils. $^1$H NMR spectra were referenced relative to $H_2O$ at δ 4.77 ppm as an internal standard. The water signal was suppressed with a 2 s presaturation pulse of 200 Hz field strength using the PRESAT pulse sequence provided in VnmrJ 3.2A. For each spectrum, 32 transients were averaged with 3 s acquisition time, 2 s relaxation delay, and 90 degree (7 μs) excitation pulse. Signals were analyzed for the presence of PEG.

Biomechanical Testing of CC-DHA

To evaluate the mechanical properties of the CC-DHA elastomer shields for translation to clinical application for the prevention of needle puncture injury, mechanical properties and needle puncture force were evaluated. Biomechanical testing was performed on CC-DHA shields using a custom built mechanical load tester. The CC-DHA shields were subjected to load-displacement compression tests to determine the average Young's Modulus as well as the average penetration force needed to break through the sample. Briefly, to create stress-strain compression curves, a small tare-load of 2 g was applied using a 10 mm-diameter non-porous plane-ended load plate to detect contact with the CC-DHA shield surface, followed by a pre-displacement of 25 μm to ensure uniform contact with the load plate. After a 10-second relaxation period, samples were compressed a displacement of 1500 μm at a step velocity of 0.1 mm/sec and the load was recorded using a 250 g load cell (resolution 0.25 g). All load, displacement, and time data were collected at a frequency of 20 Hz. Functional biomechanical properties were determined from the loading and displacement phases. Stress and strain were calculated and plotted based on dimensional characteristics of the CC-DHA. The Young's Modulus was defined as the slope of the linear portion of the stress-strain compression curves. The elastic remodeling linear portion was determined as the area of the curve that was 20%-80% of the maximum force recorded by the machine. Six shields were tested to obtain stress-strain curves. The Young's modulus was determined from the average of the respective curves.

Furthermore, to study the force required to puncture the shield in a physiologically relevant manner, the device was fitted with a needle commonly used for laparotomy fascial closure (Maxon™ 1-0 suture, GS-21 needle). The needle was positioned at a 90° angle to the material, and displaced through the sample at the same rate as previously discussed. The maximum penetration force was quantified on 2 mm thick CC-DHA specimens (81.4+/−9.4 mg). The force required to puncture the shields at 90° were recorded. All testing was also performed under identical conditions for rat small bowel, and a 0.6-mm thick rubber band (Sparco™, SPR33-11B). Means and standard deviations were used to summarize the continuous variables. A one-way ANOVA was used to compare variables among experimental groups, and statistical analyses were performed on GraphPad Prism™. A value of $p<0.05$ was considered significant.

In Vivo Degradation of CC-DHA

Three hours after peritoneal insertion, the CC-DHA shields were completely degraded grossly, with no residual material evident at 6, 9, and 24 hours following implantation. In all cases, the suture used to tag the shield was recovered. On gross visual inspection, approximately 0.5 mL peritoneal fluid was noted in the CC-DHA mice 3 hours post-implantation, which decreased to 0.3 mL six hours post implantation. No peritoneal fluid was noted 9 and 24 hours post-implantation.

In Vivo Toxicity and Peritoneal Adhesion

In the cohort of mice that received CC-DHA elastomer shields and were evaluated daily for 14 days, all animals were noted to be in good health by the institution's veterinary services as demonstrated by normal ambulation, appropriate feeding, weight maintenance, grooming, and nesting habits. No difference in behavior was noted compared to saline treated groups. At laparotomy after 14 days, no evidence of elastomer shields remained and no abnormal peritoneal fluid was observed in any of the mice. Significantly, there was no evidence of peritoneal adhesion formation, hematoma, bowel injury, abnormal scarring, or gross pathology in any mice. Histologic examination of various peritoneal lined tissues demonstrated no evidence of pathology or inflammation in mice who had elastomer shields placed compared to saline control.

CC-DHA Elastomer Metabolism Studies $^1$H NMR Spectroscopy of the fluids revealed PEG in blood, urine, and peritoneal fluid in all mice 3 hours after elastomer shield implantation, consistent with the rapid degradation profile of the material. One mouse who had an elastomer shield implanted urinated upon sacrifice (prior to collection) and thus had insufficient urine for analysis. No PEG signal was detected in the urine, blood, or peritoneal fluid in control mice that received saline placement within the peritoneum.

Biomechanical Testing

Figure 2A:
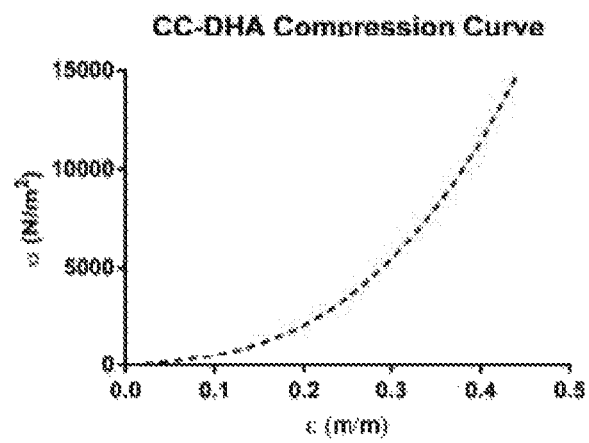
FIGS. 2A, 2B.

FIG. 2A is a plot of unconfined compression of six 8-mm diameter, 2 mm-thick CC-DHA shields. As can be ascertained from FIG. 2A, the compression testing of shields yielded a Young's Modulus of 46.4+/−9.23 kPa.

Figure 2B:
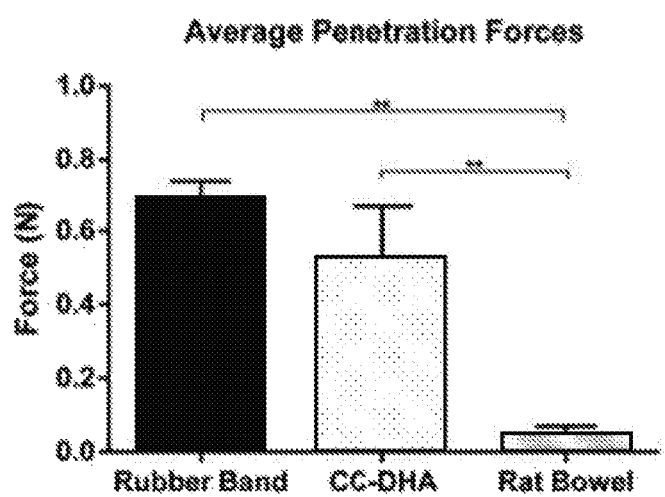

FIG. 2B is a plot of the average penetration forces for the rubber band, CC-DHA elastomer, and rat bowel. The results in FIG. 2B were obtained by a mechanical test using a puncture with GS 21 surgical needle. The maximum penetration force for a GS-21 needle applied orthogonally to the material was quantified for the elastomer, as well as for comparison materials of the rubber band and small bowel. The needle puncture forces were 0.52+/−0.16 N, 0.69+/−0.05 N and 0.048+/−0.02 N for the elastomer, rubber band and small bowel respectively, the last significantly lower than the synthetic elastomer material, $p<0.01$.

Discussion

Incisional hernia following laparotomy, with its associated morbidity, remains a significant problem after entry into the peritoneal cavity. Although there are many causes of incisional hernia, including post-operative infection and suture failure, technical/operator dependent causes, including insufficient fascial purchase, contributes significantly to this common clinical problem (e.g., Fink C, et al. Incisional hernia rate 3 years after midline laparotomy, Br. J. Surg. 2014 January; 101(2):51-4). During closure of the peritoneal cavity, prolapse of the bowel into the surgical field (especially during the final phase of closure when visualization of the bowel is limited) may cause the surgeon to take insufficient "bites" of the fascia leading to suture pull-through, fascial separation, and ultimately an incisional hernia. Further, lack of adequate visualization can result in either direct needle injury to the bowel, or strangulation of the intestine as the fascial suture is tightened, which can entrap the intestine between the suture and the abdominal wall. Although uncommon, when these injuries do occur, because of their occult nature (the surgeon often does not know the bowel is punctured or ensnared owing to poor visualization) they inevitably result in significant morbidity including bowel obstruction and necrosis, which in turn leads to spillage of bowel contents, sepsis, and even death (e.g., Margenthaler J. A., et al., Risk Factors for Adverse Outcomes Following Surgery for Small Bowel Obstruction. Ann. Surg. 2006 April; 243(4):456-64).

More recently, silicone and PVC rubber visceral shields have been introduced with some success; however, because they require removal prior to closure of the final several centimeters of fascia, the protection afforded by their use is lost at what can be considered the most critical juncture in the closure process. The present invention provides a novel implantable visceral shield, which is resilient enough to withstand inadvertent needle puncture, yet flexible enough to allow for easy placement into the peritoneal cavity while also having rapid degradation kinetics. Taken together, these characteristics represent a significant advance over the currently available devices.

The CC-DHA elastomers described herein represent a next generation of DHA-based hydrogels, as it boasts unique mechanical properties while remaining rapidly degradable under physiological conditions. Remarkably, none of the elastomer shields remained in the abdomen at 3 hours, emphasizing its rapid degradation kinetics. $^1$H NMR demonstrated the presence of PEG peritoneal fluids, blood serum, and urine as early as 3 hours after implantation, which further demonstrates the rapid hydrolysis and metabolism of the polymer. DHA is a naturally occurring molecule and readily enters metabolic pathways. The data presented herein demonstrate the rapid elimination of the remaining PEG-based degradation products, which further supports the safety of these CC-DHA elastomers in clinical use.

The polymer degraded more rapidly in vivo than in vitro, likely due to mechanical effects of the abdominal wall and visceral movement with ambulation and respiration, which further facilitates its degradation. Due to the hydrophilic nature of the CC-DHA elastomer and associated intra-abdominal osmotic gradient created by the polymer degradation, pre-operative and post-operative hydration was utilized for the mice, corresponding to that given to patients undergoing abdominal surgery.

Significantly, for clinical translation, only the diameter of the shields would need to be increased proportionally to patient size, as the elastomer thickness used in this study was sufficient to prevent inadvertent needle puncture (tested with the clinically relevant sized needles utilized in fascial closure). The large sized Glassman Visceral retainer is 16.2 cm×24.4 cm; scaling up the CC-DHA to those dimensions with 2 mm thickness would correspond to a shield of about 63 g in mass. This would correspond to a relatively minimal temporary fluid shift of approximately 0.4 L in an adult by post-operative hour 3. By comparison, during laparotomy, intravenous fluid is usually provided at a rate between 0.5-1 liter per hour. It is also possible that the thickness of the DHA shield could be further reduced, and thus, its mass and the corresponding fluid shift would be further decreased.

Visual inspection of the abdominal viscera combined with histologic analysis of the bowel substantiate the safety profile of CC-DHA. The results are consistent with the known role of DHA in glycolysis, previous work on DHA-based materials, and the FDA acceptance of polyethylene glycol, e.g., Nguyen B-C, Kochevar I. E., Influence of hydration on dihydroxyacetone-induced pigmentation of stratum corneum. J. Invest. Dermatol. 2003 April; 120(4): 655-61; Kato N, et al., Dihydroxyacetone production from methanol by a dihydroxyacetone kinase deficient mutant of *Hansenula polymorpha*. Appl. Microbiol Biotechnol. 1986 January; 23(3-4):180-6; Zalipsky S. Chemistry of polyethylene glycol conjugates with biologically active molecules. Adv. Drug Deliv. Rev. 1995 September; 16(2-3):157-82; Roberts M. J., Chemistry for peptide and protein PEGylation. Adv. Drug Deliv Rev. 2012 December; 64(SUPPL.): 116-27; and Veronese F M. Peptide and protein PEGylation. Biomaterials. 2001 March; 22(5):405-17. Furthermore, elastomer shields did not induce intra-abdominal adhesion formation when left in situ.

Most importantly, mechanical testing substantiates the hypothesis that the elastomer would protect the viscera during closure. Mechanical testing was performed using a GS-21 needle and 90° puncture angle. In clinical practice, however, the position of the needle over the viscera during closure is tangential to the horizontal. Using 45° and 30° puncture angles of the needle to the horizontal plane in which the elastomer shield would lie in clinical application as a model, the resultant tangential puncture force would translate to 0.73+/−0.23 N and 1.03+/−0.32 N, respectively, compared to the much lower force needed to penetrate rat small bowel (0.07+/−0.03 and 0.10+/−0.04 N respectively). While the force to puncture the CC-DHA with a GS-21 needle was 25% less than the rubber band, it was ten-fold higher than the force at which the bowel is punctured. In a study on larger mammals, under similar conditions, Bao et al. demonstrated a puncture force range of 0.25-0.28 N for rabbit bowel, which translates to 0.50-0.58 N at 30-45 degrees, still significantly less than that of the studied shields (Bao X, et al., Experiment study on puncture force between MIS suture needle and soft tissue. *Biosurface and Biotribology*, 2016 June; 2(2):49-58). Taken together, these data demonstrate that the CC-DHA elastomer forms a highly effective protective barrier over the viscera, with the potential for wider application in a variety of medical and surgical applications.

This application discloses a resilient and rapidly degradable biocompatible surgical device from non-toxic building blocks that can be left in situ to shield the viscera during surgical closure. Under physiological conditions, the DHA-based elastomers rapidly hydrolyze and DHA is safely eliminated from the body via a natural metabolic pathway, thereby reducing the risk of inflammation and local toxicity. This innovative CC-DHA elastomer is sufficiently strong to withstand inadvertent needle puncture with a compelling degradation profile to facilitate safe, rapid, and efficacious fascial closure. Furthermore, where conventional agents are removed and leave viscera partially unprotected during closure, CC-DHA shields can be placed to completely cover the bowel and remain in place through the entire closure, reducing the risk of injury and without causing increased peritoneal scarring or adhesions. Given these findings, and the tunable properties of DHA-derived biomaterials, the novel elastomer described herein has the potential to be utilized across multiple surgical disciplines.

While there have been shown and described what are at present considered the preferred embodiments of the invention, those skilled in the art may make various changes and modifications which remain within the scope of the invention defined by the appended claims.

What is claimed is:

1. A composition having the following chemical structure:

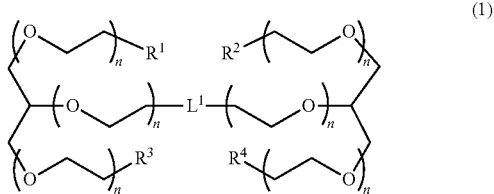

(1)

wherein:

L¹ represents a polymeric linker having the following structure:

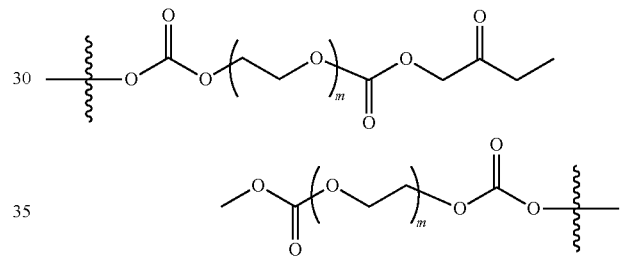

R¹, R², R³, and R⁴ are —OR', wherein R' is independently selected in each instance from hydrogen atom and hydrocarbon groups containing 1-6 carbon atoms and optionally containing one or more heteroatoms selected from N, O, S, and halogen atoms, and wherein R¹ and R² are optionally interconnected to form a polymeric linker L², and/or wherein R³ and R⁴ are optionally interconnected to form a polymeric linker L³, wherein L² and L³ are each independently represented by the structure provided for L¹, except that the subscript m is taken independently among L¹, L², and L³;

the subscript n is an integer of at least 2; and the subscript m is an integer of at least 2 and up to 10.

2. The composition of claim 1, wherein the composition of Formula (1) has the following chemical structure:

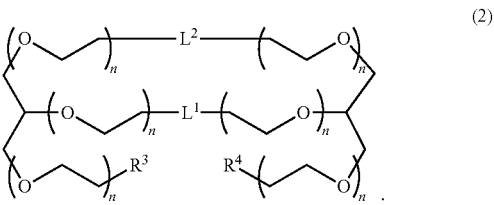

(2)

3. The composition of claim 1, wherein the composition of Formula (1) has the following chemical structure:

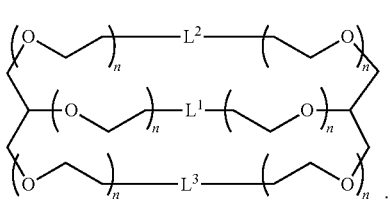
(3)

4. The composition of claim 1, wherein m is an integer of at least 2 and up to 5.

5. The composition of claim 1, wherein m is an integer of at least 3 and up to 10.

6. The composition of claim 1, wherein m is an integer of at least 3 and up to 5.

7. A surgical barrier device capable of shielding biological tissue from inadvertent needle puncture and capable of biodegrading in the biological tissue after use, the surgical barrier device comprising a film of a composition having the following chemical structure:

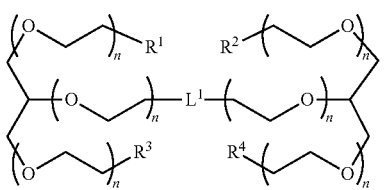
(1)

wherein:

$L^1$ represents a polymeric linker having the following structure:

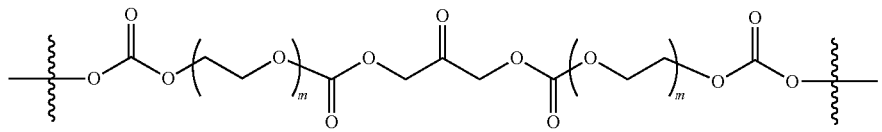

$R^1$, $R^2$, $R^3$, and $R^4$ are —OR', wherein R' is independently selected in each instance from hydrogen atom and hydrocarbon groups containing 1-6 carbon atoms and optionally containing one or more heteroatoms selected from N, O, S, and halogen atoms, and wherein $R^1$ and $R^2$ are optionally interconnected to form a polymeric linker $L^2$, and/or wherein $R^3$ and $R^4$ are optionally interconnected to form a polymeric linker $L^3$, wherein $L^2$ and $L^3$ are each independently represented by the structure provided for $L^1$, except that the subscript m is taken independently among $L^1$, $L^2$, and $L^3$;

the subscript n is an integer of at least 2; and the subscript m is an integer of at least 2 and up to 10.

8. The surgical device of claim 7, wherein the composition of Formula (1) has the following chemical structure:

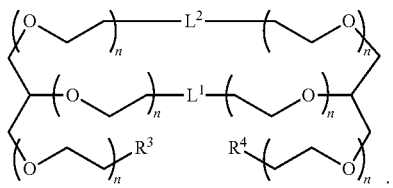
(2)

9. The surgical device of claim 7, wherein the composition of Formula (1) has the following chemical structure:

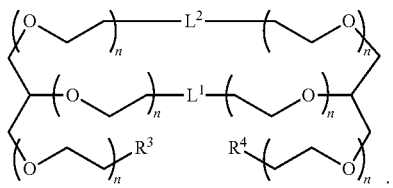
(3)

10. The surgical device of claim 7, wherein m is an integer of at least 2 and up to 5.

11. The surgical device of claim 7, wherein m is an integer of at least 3 and up to 10.

12. The surgical device of claim 7, wherein m is an integer of at least 3 and up to 5.

13. The surgical device of claim 7, wherein the film has a thickness of at least 0.5 mm and up to 5 mm.

14. The surgical device of claim 7, wherein the film has a thickness of at least 1 mm and up to 5 mm.

15. The surgical device of claim 7, wherein the film has a thickness of at least 1 mm and up to 3 mm.

16. A method of protecting bodily tissue from needle puncture during surgery, the method comprising placing a surgical barrier device capable of shielding biological tissue from inadvertent needle puncture on bodily tissue to be protected during surgery, the surgical barrier device comprising a film of a composition having the following chemical structure:

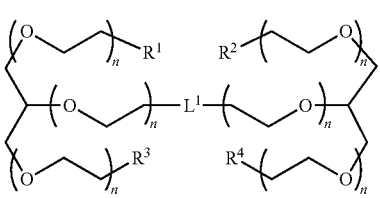
(1)

wherein:

$L^1$ represents a polymeric linker having the following structure:

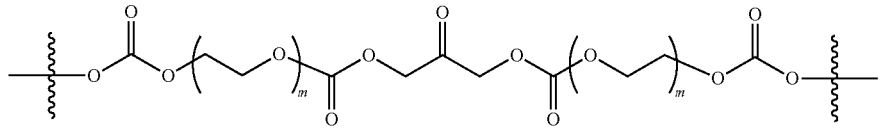

$R^1$, $R^2$, $R^3$, and $R^4$ are —OR', wherein R' is independently selected in each instance from hydrogen atom and hydrocarbon groups containing 1-6 carbon atoms and optionally containing one or more heteroatoms selected from N, O, S, and halogen atoms, and wherein $R^1$ and $R^2$ are optionally interconnected to form a polymeric linker $L^2$, and wherein $R^3$ and $R^4$ are optionally interconnected to form a polymeric linker $L^3$, wherein $L^2$ and $L^3$ are each independently represented by the structure provided for $L^1$, except that the subscript m is taken independently among $L^1$, $L^2$, and $L^3$;

the subscript n is an integer of at least 2; and the subscript m is an integer of at least 2 and up to 10; and leaving the surgical barrier device in the body after completion of the surgery, and allowing the surgical barrier device to degrade in the biological tissue and ultimately leave the body as degradation products.

17. The method of claim 16, wherein the composition of Formula (1) has the following chemical structure:

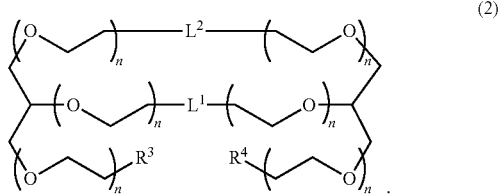
(2)

18. The method of claim 16, wherein the composition of Formula (1) has the following chemical structure:

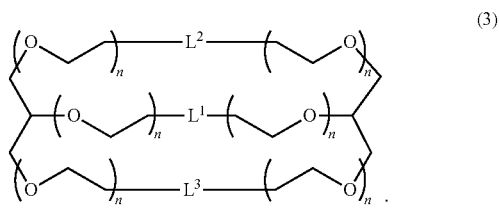
(3)

19. The method of claim 16, wherein m is an integer of at least 2 and up to 5.

20. The method of claim 16, wherein m is an integer of at least 3 and up to 10.

21. The method of claim 16, wherein m is an integer of at least 3 and up to 5.

22. The method of claim 16, wherein the film has a thickness of at least 0.5 mm and up to 5 mm.

23. The method of claim 16, wherein the film has a thickness of at least 1 mm and up to 5 mm.

24. The method of claim 16, wherein the film has a thickness of at least 1 mm and up to 3 mm.

25. The method of claim 16, wherein the surgical barrier device exhibits a degradation profile of at least 90% degradation within 4 hours of contact of the surgical barrier device with bodily fluid.

26. The method of claim 16, wherein said surgery comprises abdominal surgery.

27. The method of claim 26, wherein said abdominal surgery comprises a fascial closure.

28. The method of claim 26, wherein said abdominal surgery comprises a laparotomy.

* * * * *